US012569326B2

(12) United States Patent
Ward et al.

(10) Patent No.: US 12,569,326 B2
(45) Date of Patent: Mar. 10, 2026

(54) LAMINATED TISSUE GRAFT PRODUCT

(71) Applicant: AROA BIOSURGERY LIMITED, Auckland (NZ)

(72) Inventors: Brian Roderick Ward, Waiau Pa (NZ); Barnaby Charles Hough May, Auckland (NZ); Andrew Raymond Campbell, Wellington (NZ)

(73) Assignee: AROA BIOSURGERY LIMITED, Auckland (NZ)

( * ) Notice: Subject to any disclaimer, the term of this patent is extended or adjusted under 35 U.S.C. 154(b) by 578 days.

(21) Appl. No.: 18/116,113

(22) Filed: Mar. 1, 2023

(65) Prior Publication Data

US 2023/0200967 A1 Jun. 29, 2023

Related U.S. Application Data

(62) Division of application No. 16/727,089, filed on Dec. 26, 2019, now Pat. No. 11,617,639, which is a division of application No. 15/538,349, filed as application No. PCT/NZ2015/050215 on Dec. 18, 2015, now Pat. No. 10,548,705.

(60) Provisional application No. 62/095,493, filed on Dec. 22, 2014.

(51) Int. Cl.
| | |
|---|---|
| *A61F 2/00* | (2006.01) |
| *A61L 27/14* | (2006.01) |
| *A61L 27/36* | (2006.01) |
| *A61L 27/58* | (2006.01) |
| *B32B 5/26* | (2006.01) |
| *B32B 7/04* | (2019.01) |
| *B32B 7/05* | (2019.01) |
| *B32B 9/02* | (2006.01) |

(52) U.S. Cl.
CPC ............ *A61F 2/0077* (2013.01); *A61L 27/14* (2013.01); *A61L 27/3633* (2013.01); *A61L 27/58* (2013.01); *B32B 5/26* (2013.01); *B32B 7/05* (2019.01); *B32B 9/02* (2013.01); *A61F 2002/0081* (2013.01); *A61F 2210/0076* (2013.01); *A61F 2220/0083* (2013.01); *A61F 2250/0063* (2013.01); *B32B 2307/7163* (2013.01); *B32B 2535/00* (2013.01)

(58) Field of Classification Search
CPC ............ A61F 2/0077; A61F 2210/0076; A61F 2002/0081; A61F 2220/0083; A61L 27/3633; B32B 7/04; B32B 7/05
See application file for complete search history.

(56) References Cited

U.S. PATENT DOCUMENTS

2017/0166853 A1* 6/2017 Ekeroth ................. C12M 25/04

* cited by examiner

*Primary Examiner* — Dinah Baria
(74) *Attorney, Agent, or Firm* — Nelson Mullins Riley & Scarborough LLP; Jane E. Remillard, Esq.; Jeanne M. DiGiorgio, Esq.

(57) ABSTRACT

A tissue graft product comprising two or more layers of material wherein each layer comprises extracellular matrix (ECM) or polymeric material and wherein the layers are laminated together by interlocking portions of one layer with portions of another layer.

14 Claims, 7 Drawing Sheets

Figure 3

LAMINATED TISSUE GRAFT PRODUCT

RELATED APPLICATIONS

This application is a divisional of U.S. patent application Ser. No. 16/727,089 (now allowed) filed on Dec. 26, 2019, which is a divisional of U.S. patent application Ser. No. 15/538,349 (now U.S. Pat. No. 10,548,705) filed on Jun. 21, 2017, which claims the benefit of PCT Application No. PCT/NZ2015/050215, filed on Dec. 18, 2015, and U.S. Provisional Application No. 62/095,493, filed on Dec. 22, 2014. The entire contents of these applications are incorporated herein by reference in their entirety.

TECHNICAL FIELD

This invention relates to a tissue graft product useful in promoting the regrowth and healing of damaged or diseased tissue structures. More particularly the invention is directed to a laminated graft product formed from multiple sheets of a biological and/or synthetic material and to a method for making the product.

BACKGROUND OF THE INVENTION

Compositions of decellularised tissues from warm-blooded vertebrates, including humans, can be used as tissue graft materials. Common tissue graft compositions may be derived from the dermis, the small intestine, the urinary bladder, renal capsule, the simple glandular stomach and the forestomach matrix (see, for example, U.S. Pat. Nos. 4,902, 508, 5,554,389, 6,099,567, 7,087,089, and 8,415,159, the entire contents of which are incorporated herein by reference). These compositions are known as extracellular matrix (ECM) and have an important role in providing the optimal chemical and structural environment for tissue growth and regeneration. ECM scaffolds used for tissue regeneration are traditionally prepared from decellularised human and animal tissues isolated from various organs and from a variety of animal connective tissue and basement membrane sources. These scaffolds promote tissue regeneration and are well-tolerated immunologically.

The ideal tissue graft is one that is the closest possible analogue to native tissue. Tissue processing is required to remove cellular components that otherwise may cause rejection and to ensure safety from transmissible diseases. Further processing may be introduced to customise the fabrication of the graft to meet site specific requirements and to improve shelf life. Each successive processing step has the potential to damage the ECM, alter the immune response and consequently affect the tissue remodelling process. Chemical processing, drying and sterilisation techniques damage ECM and therefore affect the in vivo behaviour of grafts (1-3). Ready to use products are favoured by surgeons. Consequently, minimally processed wet grafts are preferable.

One limitation of some ECM graft materials is that the thickness of the graft is determined by the thickness of the tissue layer obtained from the source material. For example, the thickness of forestomach ECM sheet is limited by the thickness of the source tissue. Yet applications such as hernia repair, skin graft, dural replacement, tendon repair and reconstructive surgery often require thicker grafts to provide adequate tensile strength, biomechanical performance and biological activity.

Individual sheets of ECM tissue typically have anisotropic mechanical properties that are directionally specified by the orientation of collagen fibres within the tissue. This results in directional variability in the physical properties of native single sheets of ECM tissue. Laminated graft constructs with alternate sheets having different fibre orientations can minimise the directional variability of the construct, and result in isotropic constructs which are stronger in multiple directions.

To customise ECM grafts to meet site specific requirements it is possible to fabricate laminated graft products that comprise multiple sheets of ECM using techniques such as compression and drying, chemical cross-linking, suturing, or through the use of adhesives (see U.S. Pat. Nos. 5,885,619, 5,955,110, and 8,415,159).

Graft products made using these techniques have limitations. Where air, heat or lyophilisation is used to dry the graft products, the ECM is damaged as a consequence of water loss. In the case of lyophilisation, ice crystal formation leads to structural changes of the scaffold (4). While dehydration and compression have been used as a method to fabricate laminated graft products, the ECM proteins are typically damaged in the process and consequently elicit an exaggerated immunological response. A further limitation of dehydrated and compressed products is their tendency to delaminate after rehydration, during surgical handling, implantation and subsequently over time.

Sutures may be used to overcome the tendency of laminated graft products to delaminate. However, sutures introduce a foreign material into the graft and this can lead to inflammation, scarring and encapsulation, and may not be desirable in some situations (5). For example, fabricating a laminated ECM graft product using permanent synthetic sutures, such as Prolene, to secure the sheets together will result in the replacement of the ECM over time but the synthetic sutures will not be remodeled. This is not desirable in applications where the graft should be completely replaced by the patient's own tissue. Permanent sutures result in a greater likelihood of infection and limit the utility of this type of product in open dermal repair applications. Graft products that include absorbable sutures have a limited shelf-life in a wet presentation because the sutures often break down through hydrolysis (6,7). Consequently, in applications that require a high tensile strength over a sustained period of time, absorbable sutures are not suitable.

Laminated graft products may also be comprised of ECM sheets held together using an adhesive. However, introducing an adhesive can create a barrier to cell migration and can alter the typical mechanisms and kinetics of ECM remodelling.

Graft products that comprise chemically cross-linked sheets of ECM bound together are known to elicit a foreign body response and have limited biotrophic properties.

Graft products that are exclusively comprised of a synthetic polymer mesh are known to provide long-term strength and rigidity. However, over time the large amount of synthetic material can cause a foreign body response and may result in mesh erosion where the mesh can pass through layers of tissue. Synthetic polymer material grafts have no biological component and therefore do not provide biological assistance with wound and tissue repair. This can lead to encapsulation of the graft and increases the risk of adverse reactions.

It can therefore be seen from the problems and disadvantages associated with existing graft products that there is a need for laminated graft products that comprise ECM and/or a natural or synthetic polymer material and can be readily tuned to meet the biophysical requirements of a wide range of anatomical sites and do not delaminate during surgery or after implantation. Furthermore, a graft product that remains intact in both dry and wet presentations is desirable. A laminated graft product that can be presented in a wet form to avoid damage to the ECM and retain inherent biotrophic properties is most desirable.

It is therefore an object of the invention to provide a tissue graft product comprising two or more layers of ECM or polymeric material which overcomes, at least in part, one or more of the abovementioned problems, or to at least provide a useful alternative to existing products or procedures.

SUMMARY OF THE INVENTION

The invention provides a tissue graft product comprising two or more layers of extracellular matrix (ECM) or polymeric material without the use of any synthetic material for holding the layers together, such as sutures or adhesive, thereby minimising the risk of rejection, inflammation or undesirable encapsulation.

Accordingly, in a first aspect of the invention there is provided a tissue graft product comprising two or more layers of material wherein each layer comprises extracellular matrix (ECM) or polymeric material and wherein the layers are laminated together by interlocking portions of one layer with portions of another layer.

In certain embodiments of the invention, the tissue graft product comprises a first layer of material having multiple lugs and a second layer of material having multiple holes, each lug of the first layer being located through a hole in the second layer, the holes and the lugs having dimensions so that the lugs engage with a surface of the second layer and interlock the first layer with the second layer.

The tissue graft product may have at least one layer comprising ECM, or may have all layers of material comprising ECM. The product may comprise any suitable number of layers of ECM and/or polymeric material, for example 2, 3, 4, 5, 6, 7, 8, 9 or 10 layers of ECM and/or polymeric material. The ECM may be formed from the propria-submucosa of the forestomach of a ruminant. The tissue graft product may have at least one layer comprising polymeric material, or may have all layers of material comprising polymeric material. The polymeric material may be a synthetic material formed from polypropylene, polytetrafluoroethylene, polyglycolic acid, polylactic acid, poliglecaprone-25, or polyester. Alternatively, the polymeric material may be a natural material such as a protein, polysaccharide, glycoprotein, proteoglycan, or glycosaminoglycan. Examples may include collagen, alginate, chitosan and silk.

Each hole of the second layer may have any suitable shape including a substantially circular, triangular, square, rectangular, diamond, or star shape. Circular shaped holes typically have a diameter in the range of 2 to 4 mm. Each layer having multiple holes may have a density of holes of 0.5 to 15 holes per $cm^2$.

The tissue graft product of the invention may be a substantially flat sheet or may have a 3-dimensional form shaped to conform to a location to which the product is to be grafted.

The tissue graft product may be wet or may be dried, for example by lyophilisation.

In a second aspect, the invention provides a method of preparing a tissue graft product of the invention, comprising the step of laminating two or more layers of material wherein each layer comprises extracellular matrix (ECM) or a polymeric material and wherein the layers are laminated together by interlocking portions of one layer with portions of another layer.

In some embodiments of the invention, the method comprises the steps:
   (i) applying a first layer of material having multiple lugs to a second layer of material having multiple holes,
   (ii) pushing the lugs of the first layer through the holes in the second layer, the holes and the lugs having dimensions so that the lugs engage with a surface of the second layer and interlock the first layer with the second layer.

In another aspect of the invention, there is provided a tissue graft product of the invention, comprising:
   (i) a mould to which a sheet of ECM or polymeric material can be overlaid;
   (ii) a lug cutting means for cutting lugs into a sheet of ECM or polymeric material to form a lug sheet;
   (iii) a piercing means for creating piercings in a sheet of ECM or polymeric material to form a pierced sheet;
   (iv) a means for pushing the lugs of the lug sheet through the piercings of the pierced sheet to form the tissue graft product.

In a further aspect of the invention, there is provided the use of a graft product of the invention for replacing or repairing tissue in a human or other animal.

BRIEF DESCRIPTION OF THE FIGURES

FIG. 3 is a schematic representation of an example of tooling used to prepare a tissue graft product of the invention.

DETAILED DESCRIPTION

Definitions

Figure 1:
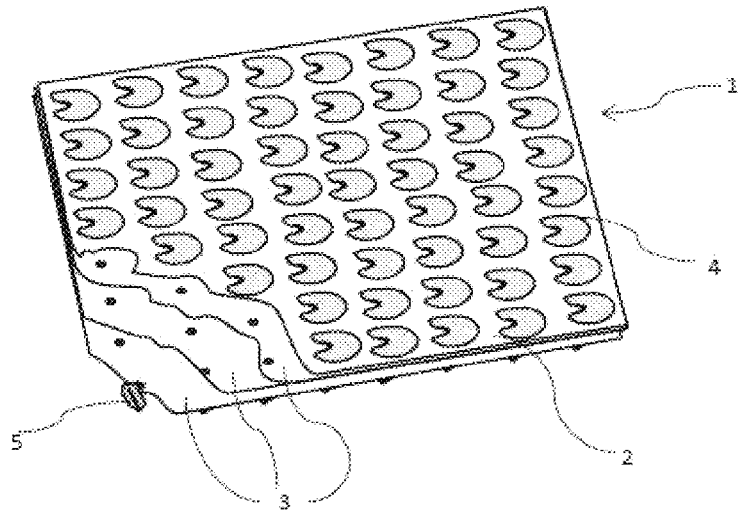
FIG. 1 is a schematic representation of a tissue graft product of the invention.

The term "extracellular matrix" (ECM) as used herein refers to animal or human tissue that has been decellularised and provides a matrix for structural integrity and a framework for carrying other materials.

The term "decellularised" as used herein refers to the removal of cells and their related debris from a portion of a tissue or organ, for example, from ECM.

The term "polymeric material" as used herein refers to large molecules or macromolecules comprising many repeated subunits, and may be natural materials including, but not limited to, polypeptides and proteins (e.g. collagen), polysaccharides (e.g. alginate) and other biopolymers such as glycoproteins, or may be synthetic materials including, but not limited to, polypropylene, polytetrafluoroethylene, polyglycolic acid, polylactic acid, and polyester.

The term "interlock" or "interlocking" as used herein refers to the engagement and fitting together of two or more overlapping sheets of material.

The term "laminate" or "laminating" as used herein refers to the overlaying of one sheet of material on another sheet of material.

The term "sheet" as used herein refers to a substantially flat flexible section of ECM or polymeric material.

The term "layer" as used herein refers to two or more sheets overlaid or adjacent to and interlocked with each other.

The term "lug" as used herein refers to a section of a sheet that has been partially cut out so that the lug remains fixedly attached to the sheet via a connection bridge.

The term "lug sheet" as used herein refers to a sheet into which multiple lugs have been cut.

The term "pierced sheet" as used herein refers to a sheet into which multiple holes have been pierced.

The term "lugging" as used herein refers to a process of pushing lugs of a lug sheet through holes of a pierced sheet.

The term "lugged sheet" as used herein refers to a lug sheet where the lugs of the lug sheet have been pushed through the holes of a pierced sheet.

Laminated Graft Product

The invention relates generally to the lamination of two or more sheets of ECM or polymeric material where the sheets are held together by interlocking portions of one sheet with portions of another sheet. Although the invention is not restricted to any particular method of interlocking, the invention will be described with reference to a method where lugs in one or more sheets have been pushed through holes in other sheets so that the sheets are interlocked and held together to form a laminated graft product. The laminated graft products of the invention provide advantages over other types of laminated products, and are useful in a variety of clinical and therapeutic applications, including wound repair and tissue regeneration and including applications such as hernia or ligament/tendon repair where additional tensile strength is required over the strength of a single sheet of ECM.

Some embodiments of the invention feature sheets laminated without the use of any additional materials, such as sutures or adhesives, or the use of drying steps in the process for their manufacture, which could adversely affect or render the device unsuitable for wound or tissue repair. These laminates have a greater tensile strength than individual sheets. They are also perforated, which facilitates the drainage of fluid, reducing the risk of seroma formation.

Some laminated products described in the prior art which have been laminated without the addition of other compositions are unsuitable for wet presentation because they tend to delaminate under extended periods of hydration. The product of the present invention does not delaminate after prolonged exposure to water and retains its structural integrity.

In general terms, the invention is based on a method comprising overlaying multiple sheets of ECM or polymeric material and interlocking portions of the sheets to form a laminated graft product.

Extracellular Matrix

ECM-derived matrices for use in the invention are collagen-based biodegradable matrices comprising highly conserved collagens, glycoproteins, proteoglycans and glycosaminoglycans in their natural configuration and natural concentration. One extracellular collagenous matrix for use in this invention is ECM of a warm-blooded vertebrate. ECM can be obtained from various sources, for example, gastrointestinal tissue harvested from animals raised for meat production, including pigs, cattle and sheep or other warm blooded vertebrates. Vertebrate ECM is a plentiful by-product of commercial meat production operations and is thus a low cost tissue graft material.

The ECM tissue suitable for use in the formation of the graft products comprises naturally associated ECM proteins, glycoproteins and other factors that are found naturally within the ECM depending upon the source of the ECM. One source of ECM tissue is the forestomach tissue of a warm-blooded vertebrate.

Forestomach tissue is a preferred source of ECM tissue for use in this invention. Suitable forestomach ECM typically comprises the propria-submucosa of the forestomach of a ruminant. In particular embodiments of the invention, the propria-submucosa is from the rumen, the reticulum or the omasum of the forestomach. These tissue scaffolds typically have a contoured luminal surface. In one embodiment, the ECM tissue scaffold may additionally contain decellularised tissue, including portions of the epithelium, basement membrane or tunica muscularis, and combinations thereof. The tissue scaffolds may also comprise one or more fibrillar proteins, including but not limited to collagen I, collagen III or elastin, and combinations thereof. These sheets are known to vary in thickness and in definition depending upon the source of vertebrate species.

Propria-submucosa tissue typically has an abluminal and a luminal surface. The luminal surface is the surface facing the lumen of the organ source and the abluminal surface faces the smooth muscle tissue surface. The multiple sheets of propria-submucosa can be overlapped with the abluminal surface contacting the luminal surface, the luminal surface contacting the luminal surface, or with the abluminal surface contacting the abluminal surface of an adjacent sheet of ECM. All of these combinations of overlapping sheets of ECM from some or different vertebrate or organ sources will produce a laminated graft product comprising ECM.

One method of preparing ECM for use in accordance with this invention is described in U.S. Pat. No. 8,415,159. A segment of the vertebrate forestomach, preferably harvested from ovine species is subjected to a transmural osmotic flow between two sides of the tissue, such that the tissue layers within all or a portion of the tissue are separated and/or decellularised. The transmural osmotic flow can be directed from the luminal to the abluminal side of all or a portion of the tissue, or from the abluminal to the luminal side of all or a portion of the tissue. This may be achieved, for example, by separating the tissue between a hypertonic solution and a hypotonic solution, such that the transmural osmotic flow is directed from the hypotonic solution to the hypertonic solution. The method may further involve removing all or part of a tissue layer including epithelium, basement membrane, or tunica muscularis, and combinations thereof. The hypertonic and hypotonic solutions may include, for example, water and optionally at least one buffer, detergent or salt. The hypertonic solution contains a higher concentration of solute than the hypotonic solution. In a particular embodiment, the hypertonic solution comprises 4 M NaCl and the hypotonic solution comprises 0.28% Triton X-200 and 0.1% EDTA. In another particular embodiment, the hypotonic solution comprises 0.1% SDS. In still another embodiment, the hypotonic solution comprises 0.028% Triton X-200, 0.1% EDTA, and 0.1% SDS. The ECM can be stored in a hydrated or a dehydrated state. Lyophilised or air dried ECM may be rehydrated or partially rehydrated and used in accordance with this invention without significant loss of its biotropic and mechanical properties.

Polymeric Materials

In some embodiments of the invention, sheets of polymeric material may be included in the product as either lug sheets or pierced sheets. For example, additional strength or longer persistence may be incorporated into the product by including a fine woven permanent synthetic material such as polypropylene (found in Prolene mesh and Elevate mesh), polytetrafluoroethylene (found in Gore-Tex mesh), polyglycolic acid (found in Vicryl mesh), polylactic acid (found in Paritex progrip mesh), poliglecaprone-25 (found in Ultrapro mesh), and polyester (found in Mersilene mesh). Synthetic materials such as polypropylene, PTFE and polyester are non-resorbable and will persist indefinitely, providing long lasting strength and rigidity. Synthetic materials such as polyglycolic acid, polylactic acid and poliglecaprone-25 are resorbable meshes and will provide additional strength in the short-term, but will resorb in the long term. Alternatively, the polymeric material may be a natural material, or derived from a natural material, such as proteins (e.g. collagen), polysaccharides (e.g. alginate), glycoproteins or other materials.

In other embodiments, the product may comprise sheets of polymeric material only (i.e. no sheet of ECM).

General Method for Preparing Graft Products

In one embodiment of this invention, laminated graft products are formed from multiple overlapped or partially overlapped sheets. The dimensions of the individual sheets used are not critical. One method of forming laminated graft products of ECM and/or SPM comprises the steps of pushing a suitably shaped cutter (lug cutter) through a sheet to form numerous lugs across the sheet to form a "lug sheet". The lug sheet may be a wet, dried, lyophilised, rehydrating or rehydrated sheet. A lug layer may comprise one or more combinations of lug sheets, which may or may not overlap each other. The lug layer may also comprise different combinations of lug sizes and in varying patterns to improve strength across multiple layers of laminates. Piercing a sharp or blunt needle through a sheet of ECM or polymeric material to form numerous small piercings across the sheet forms a "pierced sheet". A pierced sheet may be a wet, dried, lyophilised, rehydrating or rehydrated sheet. A pierced layer may comprise one or more combinations of pierced sheets, which may or may not overlap each other. The lug layer is at least partially overlaid onto the pierced layer. At this point in the method, the layers may be rehydrated with a liquid such as isotonic saline. The lugs of the lug layer are then pushed through the piercings of the pierced layer using a pin, push rod, punch, blunt needle or similar device to interlock and secure the lug layer to the pierced layer. This forms a laminated graft product of the invention.

Figure 2:
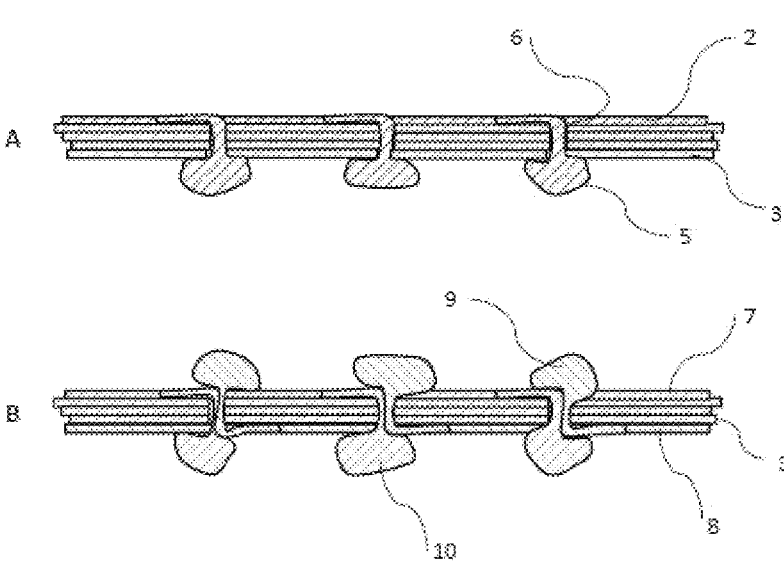
FIGS. 2A and 2B show cross-sectional views of schematic representations of tissue graft products of the invention.

Referring to FIG. 1, a laminated graft product 1 is shown comprising a lug sheet 2 and three pierced sheets 3. Each section 4 shows where a lug has been cut out from the lug sheet 2 and has been pushed through piercings in pierced sheets 3 to the underside of the graft product 1. A single lug 5 is depicted having been pushed through from the lug sheet 2. Other lugs are not shown. FIG. 2A is a cross-sectional view of a laminated graft product. A lug sheet 2 is shown overlaid on four pierced sheets 3. Lugs 5 are shown having been pushed through piercings in the pierced sheets 3 from the lug sheet 2. Each lug 5 remains attached to the lug sheet 2 via a connection bridge 6. It will be appreciated that in practice each lug 5 will lie substantially flat against the underside of the graft product 1. All sheets are therefore interlocked and held together.

In some embodiments of the invention, the laminated graft product consists essentially of ECM tissue, free of potentially compromising sutures, adhesives and chemical pre-treatments, and has a greater mechanical strength and collagen content per $cm^2$ than the individual sheets used to form the product.

The amount of tissue overlap between adjacent sheets can be varied depending on the intended use, desired properties, required lamination strength, required surface area or size of the product, provided that at least a portion of each sheet overlaps and interlocks with a portion of another sheet. The lugs interlock and secure pierced sheets to the lug sheets in overlapping regions to give a laminated graft product.

The term "interlocking" or "interlock" as defined above refers to the way in which one or more lug sheets secure one or more pierced sheets together without the need for the addition of other materials such as adhesives or sutures, or the need for treatments such as compression and dehydration. Products formed may vary in the number of layers and sheets superimposed at and secured at different points of the laminated graft product. The variable structure of the graft products can provide enhanced mechanical strength.

The strength of the interlocked sheets of the product is dependent mainly on the surface area of overlapping lugged and pierced sheets, the density of fixation, the strength of the lug connection bridge, the rigidity and resistance to compression of the lug, the strength of holes in the pierced sheets and the tightness of fit between the lugs and piercings. The layers of a product with smaller piercings and larger lugs will be secured with greater strength and will therefore have a reduced likelihood of lug pull-out. However, piercings that are too small may prevent simple lug push-though (lugging) and may be prone to failure due to tearing of the pierced hole.

In preferred embodiments of the invention, the lug sheet comprises lyophilised tissue and can be hydrated once overlaid on a pierced sheet prior to pushing the lugs through the pierced sheet. However, in other embodiments, the lug sheet may comprise wet, dried, rehydrating or rehydrated sheet, or combinations thereof, provided that the lug sheet has sufficient properties to resist tearing, piercing or other deformation that would otherwise be detrimental to the process of lug cutting and lug push through, and so that lugs do not deform and slip back out through piercings.

In some embodiments of the invention, the pierced sheet comprises wet tissue. However, in other embodiments, the pierced sheet may comprise dried, lyophilised, rehydrating, rehydrated sheet, or combinations thereof, provided that the pierced sheet has sufficient properties to resist tearing or other deformation that is detrimental to piercing, lug push through or lug holding.

Tooling for Preparing Graft Products

In a typical method for preparing a graft product of the invention, the sheets used to prepare the lug and pierced sheets of the present invention are placed onto a mould. In one embodiment, the sheets can be stretched in both a longitudinal and lateral direction on a mould in order to create tension in the sheet to allow for effective lug formation, piercing and/or lug push through. The stretched sheet is punctured by and placed over sharp or blunt pins around the perimeter of the mould to maintain tension in the stretched sheet. Alternatively, sheets can be stretched and placed onto the mould and the tension in the sheets maintained using clamps or a press, or other suitable methods.

Guides such as rods, bars or similar shaped devices can be passed through the stretched sheet into the mould to secure the stretched tissue to the mould and to provide a method for aligning any subsequent sheets that are added. These guides can also be used for aligning the tools used in the process, including the tools used to produce the piercing and to push the lugs through. The use of a mould with guides in this way ensures that lugs in the lug sheet and piercings in pierced sheets are aligned above and below each other, and that the lug push through tool can also be aligned over and guided through the pierced holes.

In some embodiments, sheets are placed onto moulds and clamped in place using rods, bars or similar shaped devices which can be passed through unstretched/tension free sheets. In some embodiments, a sheet is placed onto a mould and is fixed using methods including but not limited to clamps or a press.

The composition of the mould is not critical and can be designed in any size or shape. In one embodiment, the mould is a 16 mm thick acetal block. The mould contains clearance holes for lugs, needles and pins to pass into the mould. The density, shape, size, orientation and format of the arrangement of clearance holes and the size, orientation, shape and format of the clearance holes themselves can be tailored to the type, thickness and number of sheets and layers of material, and the required application. In one embodiment, clearance holes are arranged in horizontally and vertically aligned rows and are 3.1 mm in diameter, spaced at centres of 3.5 mm. In another embodiment, clearance holes are arranged in offset horizontal or vertical rows to enable a reduction in the force required for lug cutting and/or to allow a high density of lugs and fixation points.

In another embodiment, the mould is made from a group of small diameter rods with the ends of the rods forming the mould surface. In such an embodiment, the rod tips move to allow passage of the lugs, needles and/or pins. In another embodiment, the mould is made of foam that parts to allow the passage of the lugs, needles and/or pins. In these embodiments, it is unnecessary to align the mould with the process tooling.

In some embodiments, the mould has a flat planar surface and is used to form planar laminated graft products.

In a typical process, a sheet of ECM or polymeric material is placed on the mould and lugs are cut with a suitably shaped cutter (lug cutter) to form a lug sheet. The lug sheet is removed and a new sheet of ECM or polymeric material is placed on the mould. Alternatively, a new sheet is placed on a different mould having a similar clearance hole and guide pattern. The new sheet is pierced using a needle or multiple needles to form a pierced sheet. Subsequently, one or more lug sheets are overlaid on to a layer of one or more pierced sheets and the lugs of the lug sheet are pushed through the layer of pierced sheets using a non-sharp (blunt end) pin or multiple pins. Once the lugs have been pushed through the holes of the pierced sheets, the lugs tend to open out thereby interlocking the lug sheet and pierced sheets together to form the laminated graft product. Graft products may be prepared having at least two sheets, but may comprise 3, 4, 5, 6, 7, 8, 9, 10 or more sheets.

When wet sheets are used, a separation slip may be employed between either of the sheets, lug sheets, pierced sheets and the tooling components. This reduces surface tension enabling the tooling components to be more easily parted from the sheets and other tooling components without exerting significant force on the sheets. The separation slip is typically made of a thin, flexible material, such as polytetrafluoroethylene (PTFE) or stainless steel, which can be rolled or peeled away from the sheets to remove it without creating a significant force on the sheets.

A hold down plate may be used to secure tissue prior to lug cutting, piercing and pressing of lugs through pierced sheets. In some embodiments, the lug cutters may be knives made from sharp metal tubes. In other embodiments, they may be made of any material which can be sharpened into a blade. Lug cutters cut lugs into a circular shape but may also be cut in any other shape such as, but not limited to, a square, rectangle, triangle or an inverted triangle, diamond, star, leaving a connection bridge attached to the sheet.

In some embodiments, the lugs are as small as possible so that the protruding free tips of the lugs are the least intrusive. But the lugs must have sufficient width in order to achieve a hold. For example, a lug sheet with a lug size of 2.8 mm across, spaced at centres of 3.5 mm, is preferred for preparing a 5-sheet product comprising forestomach propria-submucosa ECM sheet. The connection bridge of each lug is preferably as narrow as practicable while still surviving the lug push through operation. For a 5-sheet product comprising forestomach propria-submucosa ECM, a connection bridge of 0.7 mm wide is ideal. A smaller width of lugs and connection bridges may be suitable for laminating a smaller number of sheets, or for thinner sheets, or for the use of a more rigid lugging material. A larger lug and connection bridge width may be more suitable for laminating a larger number of sheets, thicker sheets, more flexible materials or where the presence of larger free lug tips is not a concern.

In some embodiments, lug sheets are created by cutting lugs using multiple lug cutters arranged in a flat block. The pattern of lug cutters will match clearance holes on the mould. This lug cutting block is lined up with guides and clearance holes on the mould and pressure applied to the block to cut lugs in the secured sheet on the mould to form a lug sheet. A biasing force to apply pressure can be generated by any number of suitable methods including hand force, applying a weight, an electronic press, or an hydraulic press. The lug cutting operation can be applied multiple times on large sheets to create a larger lug sheet. In other embodiments, the lug cutters may be used individually, arranged in a flexible sheet, attached to a robotic arm, or lugs may be cut using other cutting tools such as, but not limited to, a die or laser.

In some embodiments, the piercing operation may be carried out using a polished, sharp needle with a long taper. For the lamination of a 5-sheet product comprising forestomach propria-submucosa ECM sheet where one sheet is a lug sheet having 2.8 mm wide lugs spaced at centres of 3.5 mm between lugs, and having 0.7 mm wide connection bridges, a needle with a diameter of 1.2 mm, spaced with 3.5 mm centres may be used to pierce the sheets and create the holes. However, needles having a diameter of up to and even larger than 1.8 mm may produce adequate interlocking in the finished product. A smaller needle diameter may be suitable for interlocking using a lug of smaller width or where the lugging material is more flexible.

In some embodiments, pierced sheets are created by puncturing a sheet with a needle. Multiple needles may be arranged in a flat block. The pattern of needles will match clearance holes on the mould. In a similar manner to the application of force to cut lugs in a sheet to form a lug sheet, force is applied to the needle block to pierce small holes in the sheets.

The laminated product is formed by partially or completely overlapping and aligning one lug sheet over a layer of one or more pierced sheets and performing the lugging operation. In some embodiments, one lug sheet is lugged on top of one or more pierced sheets. Lugs and piercings on the lug and pierced sheets can be aligned by any suitable method including, but not limited to, by eye, using guides or using a jig. The interlocked laminated graft product is formed by pushing the lugs through the piercings to secure the layers and sheets together.

In some embodiments, the lugging operation is carried out using one or more blunted, rounded, and/or non-sharp pins (push-through pins). For the lamination of a 5-sheet product comprising forestomach propria-submucosa ECM having one lug sheet with 2.8 mm wide lugs, spaced at centres of 3.5 mm, 0.7 mm wide connection bridges and piercings made with 1.2 mm diameter needles, lugs may be pushed through using a push-through pin of 0.55 mm diameter. However, push-through pins up to and larger than 1 mm diameter will produce adequate interlocking.

In some embodiments, multiple push-through pins are arranged in a flat block in a pattern that matches the pattern of clearance holes on the mould. This pin block is lined up with guides and clearance holes on the mould and a biasing force is applied to the block to push lugs of the lug sheet through one or more pierced sheets and into the clearance holes, leaving the lugs in this position after the pins are retracted and removed from the sheet. This results in a graft product where pushed lugs anchor the one or more pierced sheets to the lug sheet. The lugging operation can be applied multiple times on large laminates to create a larger laminated sheet.

Figure 3:
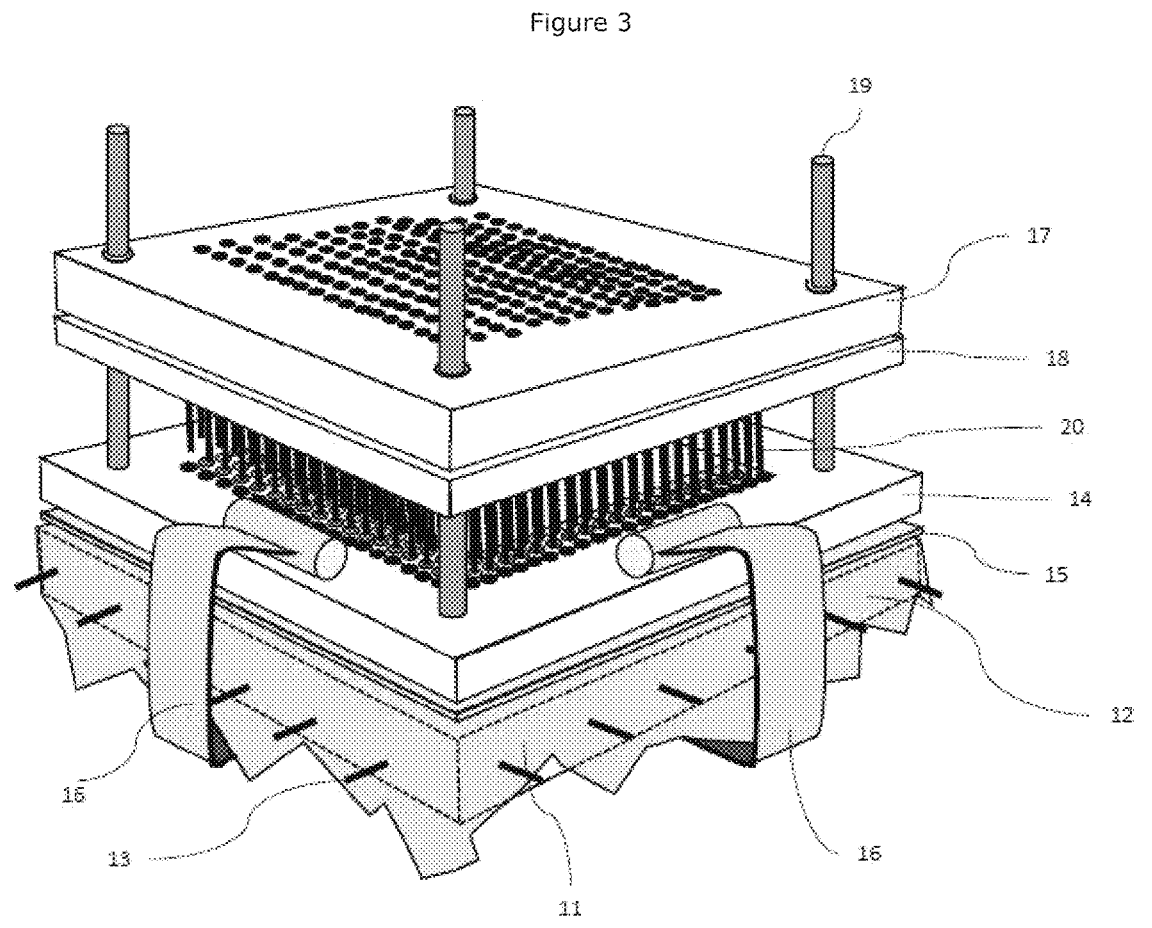

FIG. 3 is a schematic representation of an example of tooling used to prepare a tissue graft product of the invention. A mould 11 (in dotted line) is shown overlaid with a sheet 12 of ECM or polymeric material attached to the mould 11 using mould perimeter pins 13 to maintain tension in the sheet 12. A hold down plate 14 and separation slip 15 are shown clamped to the mould 11 with clamps 16. A piercing needle block 17 (which alternatively may be a lug cutter block, a piercing needle block or a push-through pin block) and a spacer block 18 may be guided onto the mould 11 using guide rods 19. Needles 20 are held by the block 17 protruding from its underside. When downward pressure is applied to piercing needle block 17, the needles 20 are forced downward to pierce the sheet 12. The piercing needle block 17 may be replaced with a lug cutter block having lug cutters protruding from its underside. In a similar operation, when downward pressure is applied to the lug cutter block, the lug cutters are forced downward to cut lugs into a sheet. Further, the piercing needle block 17 may instead be a push-through pin block having push-through pins protruding from its underside. When downward pressure is applied to the push-through pin block, the push-through pins are forced downward to push the lugs through piercings in the sheet to give the interlocked laminated graft product of the invention.

Figure 4:
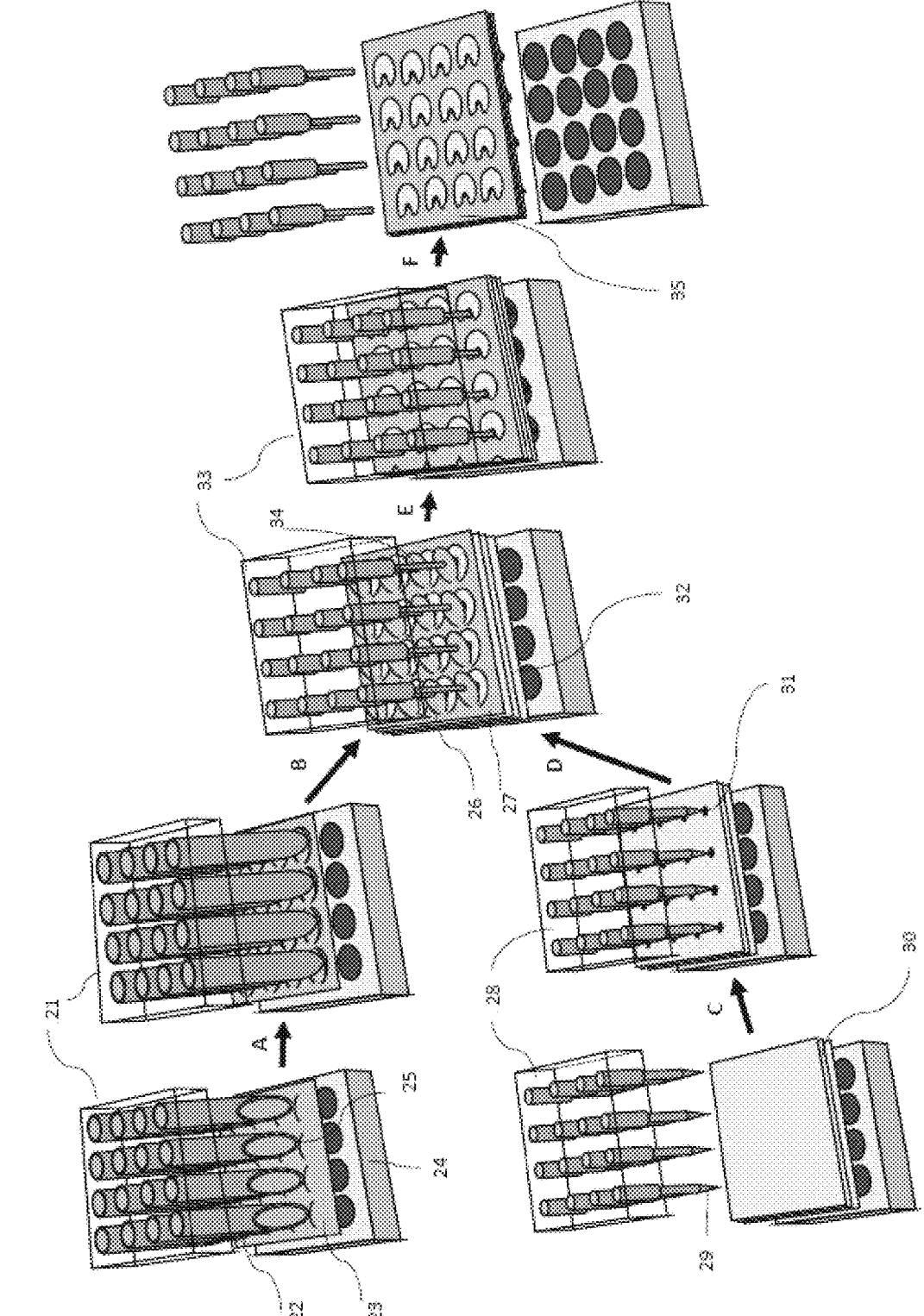
FIG. 4 shows a process for preparing a tissue graft product of the invention.

FIG. 4 shows a process for preparing a tissue graft product of the invention. Steps A and B show the preparation of a lug sheet. Steps C and D show the preparation of pierced sheets. Steps E and F show the construction of the laminated graft product. A lug cutter block 21 holds multiple lug cutters 22. The ends of lug cutters 22 have been cut at an angle so that when pressed through the sheet 23 of ECM or polymeric material held on a base 24 semi-circular cuts 25 are made in the sheet 23. The lug cutter block 21 is raised to withdraw the lug cutters 22 from the sheet 23, rotated 90° and forced downward to again cut the sheet 23. This is a repeated a second time so that the three-step procedure results in lugs 26 having been cut to form lug layer 27. Referring to step C, a piercing needle block 28 holding needles 29 is shown positioned above three sheets 30 of ECM or SPM. The piercing needle block 28 is forced downward so that multiple piercings 31 are made in the sheets 29 to form pierced layer 32. Lug layer 27 is overlaid on the pierced layer 32. A push-through pin block 33 holding multiple push-through pins 34 is forced downward so that the push-through pins 34 push the lugs 26 through the piercings 31 to interlock the pierced layer 32 with the lug layer 27 and form the laminated graft product 35.

Graft Products Comprising Multiple Sheets

In some embodiments the product formed may comprise multiple lug sheets. Sheets may be created that have a lug pattern arrangement which is offset to the lug pattern of other lug sheets. This avoids lugs on different lug sheets being arranged on top of each other and lugs being pushed through lug holes of overlapped lug sheets. These lug sheets can contain piercings to allow lugs to be pushed through lug sheets and into the pierced sheets. Sheets designed with lugs and piercings with different patterns are termed "differential lug/pierced sheets".

In other embodiments, a layer comprising one or more lug sheets and/or differential lug/pierced sheets may be placed over and under a layer of one or more pierced sheets, effectively sandwiching a layer of one or more pierced sheets between layers of sheets which contain lugs. The result is a thicker and stronger product. The sandwiched laminated graft product is formed by pushing lugs through piercings to secure the layers to form a sandwich. The lugs in the overlying lug layer are pushed through piercing s from the top and lugs in sheets of the underlying lug layer are pushed through piercings from the bottom. Lugs may or may not be pushed through all of the piercings and may or may not be pushed through the lug sheet or differentially lug/pierced sheet on the opposing side.

Referring to FIG. 2B, three pierced sheets 3 are shown sandwiched between a top lug sheet 7 and a bottom lug sheet 8. Lugs 9 from lug sheet 8 have been pushed through the piercings of the pierced sheets 3 and lugs 10 from lug sheet 7 have also been pushed through the piercings of the pierced sheets 3.

In a sandwiched product, lugs in overlying and underlying lug sheets and/or differential lug/pierced sheets may be offset against each other so that lugs from opposing sides do not come into contact. A sandwiched product in which lugs are not pushed through all layers or sheets provides advantages in situations where exposed lugs may cause tissue abrasion and/or friction. Therefore, a sandwiched device is ideal when the lug sheet and/or differential lug/pierced sheets comprise synthetic materials that are likely to be more rigid and have a greater potential to be abrasive against tissue.

Pseudoisotropic Graft Products

In some embodiments, a pseudoisotropic laminate graft product is prepared from multiple sheets of ECM. The term "pseudoisotropic" as used herein refers to a tissue graft material having similar physical properties along each axis of the graft material. The pseudoisotropic laminate graft products of the invention may be prepared from individual sheets of ECM. ECM material is typically stronger in one direction relative to other directions. This is often due to the alignment of polymer fibres (e.g. collagen) in the ECM. The method of preparing the pseudoisotropic laminate graft constructs comprises overlaying at least a portion of a first sheet of lug or pierced sheet with a second sheet of lug or pierced sheet, where the second sheet is rotated so that the longitudinal axis of the first sheet is at an angle relative to the longitudinal axis of the second sheet. Additional sheets of lug or pierced sheets can be added in a similar manner to create a pseudoisotropic laminate graft construct having the desired number of laminate sheets.

Large Area Graft Products

Large area graft products can be prepared according to the invention. Since ECM is obtained from the tissue of certain animal organs there are limitations on the size of sheets of tissue that can be used for grafting operations. When large area sheets of graft tissue are required (e.g. for large burn wounds) sutures, adhesives or other types of treatments must be used to create graft products having a sufficient surface area. However, interlocking partially overlapping sheets of ECM according to the invention enables the preparation of laminated graft products having a surface area larger than the surface area of any individual sheet used to prepare the graft product.

Three-Dimensional Graft Products

In some embodiments, the graft product is essentially a flat flexible product and has been prepared using a flat planar mould. In other embodiments, the graft product may have a curved three-dimensional shape. The ability to form three-dimensional shapes from sheets using curved moulds and lugging the sheets so that they retain their shape without having to introduce other materials or use other treatments overcomes limitations of existing technologies and is advantageous as it allows the creation of laminated products that conform more closely to the natural shape of parts of the human body. Flat laminated graft products have a limited ability to conform to a naturally curved shape, such as a breast implant, and may be prone to forming folds or creases. These creases can become sites of seroma formation leading to complications or poorer cosmetic outcomes. Therefore, the ability to form a device into a three-dimensional conformed shape during the interlocking process is advantageous.

Three-dimensional shaped interlocked laminated graft products may be formed using a mould with a curved shape. Moulds may also have stepped edges or multiple flat surfaces arranged at different angles. The mould may have non-perpendicular clearance holes for use with non-perpendicular lug cutters, needles and pins.

The lug and pierced sheets are preferably hydrated during the manufacturing process so that the tissue can more easily be conformed to the preferred shape.

A mould with clearance holes perpendicular to the mould surface may be used with an individual lug cutter, lug cutters in a flexible sheet, lug cutters on a robotic arm, a laser or other technologies. In another embodiment, a lug cutting block may be used with a mould having clearance holes which are arranged non-perpendicular to the surface. Alternatively, three-dimensional shapes can be formed by moulds with multiple flat surfaces and a lug cutting block matching the individual flat surfaces. Similarly, a mould with clearance holes perpendicular to the mould surface may be used with an individual needle, needles in a flexible sheet, a needle or needles on a robotic arm, a laser or other technologies. In another embodiment, a needle block may be used, with a mould having clearance holes which are arranged non-perpendicular to the surface. Alternatively, three-dimensional shapes can be formed by moulds with multiple flat surfaces and a needle block matching the flat surfaces. In the same manner, a mould with clearance holes perpendicular to the mould surface may be used with an individual pin, pins in a flexible sheet, a pin or pins on a robotic arm, or lugs may be pushed through piercings using other tools such as, but not limited to, a push rod, punch, die or any non-sharp object. In another embodiment, a pin block may be used, with a mould having clearance holes which are arranged non-perpendicular to the surface. Alternatively, three-dimensional shapes can be formed by moulds with multiple flat surfaces and a pin block matching the flat surfaces.

The graft product may be removed from the mould and clamps by manual force or excess tissue can be cut away from the clamps and the product can be removed from the mould. Once the product is removed from the mould, it may be dried, lyophilised, or completely hydrated or may remain in the same hydration state as when undergoing the lamination process, all without risk of delamination. The product may be further manipulated to suit various medical applications. The product can be sterilised using standard techniques.

The mechanical properties of the product can be tailored to the medical application needs by adjusting the number of layers, sheets within layers, types of sheets within layers, modifying the shape, adjusting the lugging pattern, size, density and shape, selection of ECM sheets from varying animals and tissue sources, and the selection of SPM sheets.

Perforations enhance the in vivo remodelling properties of the grafts. Perforations are believed to promote contact of the ECM tissue with endogenous fluids and cells (by increasing the surface area of the implanted graft). Perforations also serve as a conduit allowing extracellular fluid to pass through the graft. Perforations formed during the manufacture of the graft product of the invention will alleviate the accumulation of fluids between the sheets of the graft constructs by providing a conduit through which the fluid can flow out of the tissue.

Figure 5:
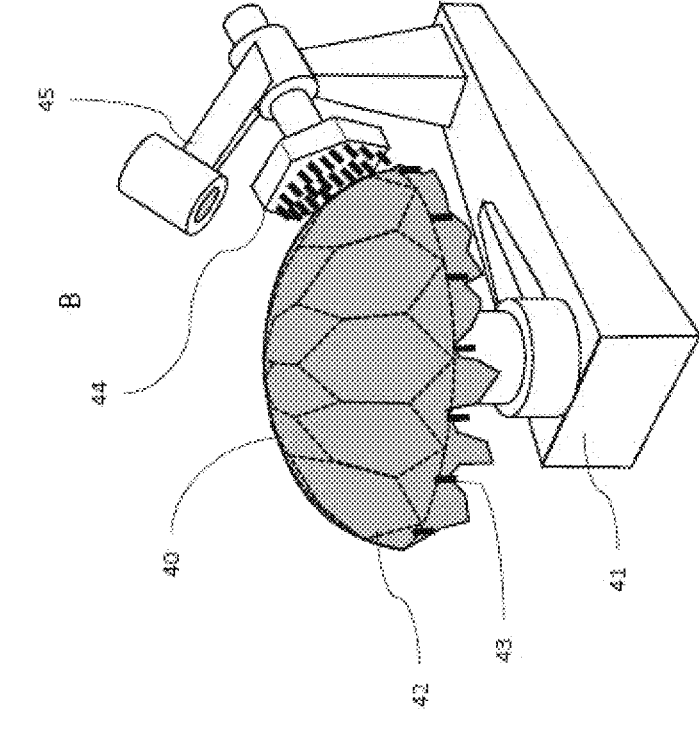
FIG. 5 is a schematic representation of an example of tooling used to prepare a three-dimensional tissue graft product of the invention.

FIG. 5 shows an example of tooling used to prepare a 3D tissue graft product of the invention. FIG. 5A shows a mould 36 on a stand 37. The mould 36 comprises multiple clearance holes 38 for receiving a needle or pin. Securing pins 39 are shown on the edge of the mould 36 to which a sheet of ECM or SPM may be secured. FIG. 5B shows an alternative arrangement using multiple needles or pins. A mould 40 is shown on a stand 41. A sheet 42 of ECM or SPM is shown stretched over the mould 40 and secured by attachment to securing pins 43. A piercing needle block 44 (which can be replaced by a push-through pin block) is attached to a block guide 45.

Delivery of Bioactive Materials

Laminated graft products of the invention may be used to deliver bioactive materials to the graft site. The bioactive materials may be endogenous to ECM used in the preparation of a graft product or may be materials that are incorporated into the ECM and/or polymeric material layers during or after the graft product manufacturing process. Bioactive materials delivered to the graft site in this way are known to be beneficial for promoting cellular function including wound healing and other desirable physiological and pharmacological functions.

EXAMPLES

Example 1: Basic Laminated Product Having One Lug Sheet and Four Pierced Sheets

ECM was prepared from vertebrate forestomach tissue in accordance with the procedure described in U.S. Pat. No. 8,415,159. Sheets of forestomach ECM were formed from a segment of forestomach tissue of a warm-blooded vertebrate, said segment comprising the propria-submucosa.

A lug sheet was prepared according to the following method: four 5 mm diameter holes were punched into one sheet of lyophilised ECM, using cutting die and press, at each corner of 140 mm×140 mm square. This sheet was placed over a 140 mm×140 mm flat acetal plate with 5 mm diameter guide rods positioned equidistant from each corner to match the holes cut into the lyophilised ECM, the guide rods fixing the sideways position of the ECM on the plate. The plate has a 29 row by 29 column grid of 3.1 mm diameter clearance holes positioned at 3.5 mm centres at its centre, resulting in a perimeter section without holes of around 20 mm wide. This plate functioned as a mould. A hold down plate with guide holes for the lug cutters and matching the pattern of clearance holes was placed on top of the lyophilised ECM sheet. Clamps were applied to secure the assembly together. A 5 mm thick spacer plate with a clearance hole size and pattern matching the guide rod holes and the clearance holes was placed on top of the hold down plate. A lug cutting block comprising an acetal block with 2.5 mm diameter circular tube lug cutters spaced at centres of 3.5 mm, matching the pattern of clearance holes was used, using guide rod holes in the acetal block and the lug cutter guide holes to align the lug cutting block when pushing the lug cutters through the ECM sheet. The assembly was placed in an arbour press and was compressed. The lug cutting block was retracted and removed, rotated 180 degrees and replaced. The assembly was placed into an arbour press and compressed. The lug cutting block was retracted and, together with the spacer, removed. The lug cutting block was rotated 90 degrees and replaced. The so formed lug sheet, with lugs of around 2.8 mm wide, was removed from the tooling.

Pierced sheets were prepared according to the following method: Four overlapping sheets of fresh ECM were stretched over a flat acetal plate having the same dimensions, holes and guide rods as the plate described above. The plate also had pins protruding from its sides which were used to secure the stretched fresh ECM sheets to the plate. A 5 mm diameter metal punch/guide was placed into each guide rod hole, through the fresh ECM, piercing the tissue and securing the tissue in place. A 1 mm thick PTFE separation slip was placed over the fresh ECM. A hold down plate also possessing a grid of holes of size and pattern matching that of the guide rod and clearance holes was placed on top of the PTFE slip. Clamps were applied to secure the assembly together. A piercing needle block comprising an acetal block with size 11 embroidery machine needles placed in a grid of pattern matching the clearance holes was used. The piercing block also had guide holes aligning with the guide rods, using these to align the piercing needle block over the mould with the needles facing towards the ECM sheet. The assembly was placed in an arbour press and was compressed. The piercing block, clamps hold down plate and PTFE separation slip were removed.

The laminated graft product was assembled by the following method: The lug sheet was placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm interlocked laminate graft construct which was moist and flexible with the appearance of a thick rough sheet. The sheet was subsequently lyophilised to produce a rigid multiply device.

Example 2: Laminated Product Having Two Lug Sheets and Three Pierced Sheets

Sheets of ECM were prepared as described in Example 1. Two lug sheets and three pierced sheet were also prepared as described in Example 1. The laminated product was assembled by the following method: Two lug sheets were placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm laminated product that was moist and flexible having the appearance of a thick rough sheet.

Example 3: Laminated Product Having a Polypropylene Lug Sheet

Sheets of ECM were prepared as described in Example 1. A lug sheet was prepared as described in Example 1 except that the sheet used was polypropylene mesh. Pierced sheets were prepared as described in Example 1. The laminated product was prepared by the following method: The polypropylene lug sheet was placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm interlocked laminate graft construct which was moist and very flexible with the appearance of a thick rough sheet.

Example 4: Laminated Product Having Different Sheets

Sheets of propria-submucosa ECM were prepared as described in Example 1. A lug sheet of lyophilised forestomach ECM was prepared as described in Example 1. Four pierced sheets were prepared according to the method of Example 1; one composed of small intestinal propria-submucosa, one composed of polypropylene mesh, one composed of pericardium and one composed of renal capsule matrix. The laminated product was assembled by the following method: The lug sheet was placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm laminated product that was moist and flexible with the appearance of a thick rough sheet. The sheet of polypropylene was sandwiched within the product, so as to not give the appearance of a synthetic product, and reduce the exposure of the synthetic material at the tissue interface, while providing the benefits of increased material strength and rigidity.

Example 5: Laminated Product Having Offset Rows of Lugs

Sheets of ECM were prepared as described in Example 1. A lug sheet of lyophilised ECM was prepared according to the method of Example 1 except that the acetal plate used has the centres of clearance holes arranged in a hexagonal lattice, each consecutive row of clearance holes staggered to do so, providing a denser clearance hole pattern over a straight column square packing arrangement. The resulting lattice of holes consists of 33 rows alternating between containing either 28 or 29 clearance holes. The plate has a perimeter section without holes of around 20 mm wide. Four overlapping pierced sheets of fresh ECM were prepared according to the method of Example 1. The laminated product was assembled by the following method: The lug sheet was placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm laminated product that was moist and flexible with the appearance of a thick rough sheet. Due to the offset row pattern of clearance holes, the force required to undertake the lug cutting, piercing and lugging operations was reduced.

Example 6: Laminated Pseudoisotropic Product

Sheets of ECM were prepared as described in Example 1. A lug sheet of lyophilised ECM was prepared according to the method of Example 1. Four overlapping pierced sheets of fresh ECM were prepared according to the method of Example 1 except that they were arranged with their collagen fibre directionality at close to 36°, −72°, +72° and −36°, relative to a lug sheet placed at 0°. The laminated pseudoisotropic product was assembled by the following method:

The lug sheet was placed on top of the pierced sheets, guiding the four guide holes down the guide rods to align. The lug sheet was rehydrated with an isotonic saline solution. The separation slip, hold down plate and clamps were replaced. A pin block comprising an acetal block with blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was removed, replaced and compressed in an arbour press a further two times. The assembly was dissembled. A scalpel was used to cut the device away from the mould. This produced a 100 mm×100 mm laminated pseudoisotropic product that was moist and flexible with the appearance of a thick rough sheet. Due to the varying fibre orientations of the individual sheets, the product had the appearance of a pseudoisotropic device with similar biomechanical properties in multiple planar directions.

Example 7: Laminated Product Having Pierced Sheets Sandwiched Between Lug Sheets Sheets of ECM were prepared as described in Example 1. Two lug sheets of lyophilised ECM were prepared according to the method of Example 1. Four overlapping pierced sheets of fresh ECM were prepared according to the method of Example 1 except that one lug sheet was placed with the free ends of the lugs at an angle of 0° on acetal plate, before stretching the four overlapping sheets of fresh ECM over the mould. The result was a pierced sheet comprising four ECM layers stretched over the mould with lugs pushed into clearance hole cavities. The laminated sandwich product was assembled by the following method: The second lug sheet was placed on top of the pierced sheets with the free end of the lugs at an angle of 180° relative to the first lug sheet, guiding the four guide holes down the guide rods to align. The lug sheet was rehydrated with a saline solution. The separation slip, hold down plate and clamps were replaced. A pin block comprising an acetal block with blunted pins, arranged in a grid matching that of the clearance holes but offset 0.5 mm from the centres of the clearance holes and aligned so that the pins were positioned furthest away from the free end of the lugs on the second lug sheet was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was retracted, replaced and compressed in an arbour press a further two times. The assembly was removed from the arbour press and turned over.

A second pin block comprising an acetal block with blunted pins, arranged in a grid matching that of the clearance holes but offset 0.5 mm from the centres of the clearance holes and aligned so that the pins were positioned furthest away from the free end of the lugs on the first lug sheet was used. The pin block also had guide holes aligning with the guide rods and was lowered on top of the mould, with the pins facing towards the ECM sheet, using the guide holes and guide rods to align. The assembly was placed in an arbour press and was compressed. The assembly was removed from the arbour press, the pins blocks on either side of the resulting construct retracted and removed, the clamps and hold down plate removed, and the separation slip removed. A scalpel was used to cut the device away from the mould. This produced a 100 mm×100 mm laminated sandwich product that was moist and very flexible with the appearance of a thick rough sheet.

Example 8: Laminated Product Having Pierced Sheets Sandwiched Between Lug Sheets but with Lugs Hidden within Product Sheets of ECM were prepared as described in Example 1. Two lug sheets of lyophilised ECM were prepared, one according to the method of Example 1 and one according to the same method except that the mould comprised a 20 row by 20 column grid of 3.1 mm diameter clearance holes positioned at 5.0 mm centres at its centre, resulting in a perimeter section without holes of around 21 mm wide. Four overlapping pierced sheets of fresh ECM were prepared according to the method of Example 1 except that one lug sheet was placed with the free ends of the lugs at an angle of 0° on acetal plate, before stretching the four overlapping sheets of fresh ECM over the mould. The result was a pierced sheet comprising four ECM layers stretched over the mould with lugs pushed into the clearance hole cavities. The laminated sandwich product was assembled by the following method:

A pin block comprising an acetal block with a 21 row by 21 column array of blunted pins, arranged in a grid matching that of the clearance holes was used. The pin block also had guide holes aligning with the guide rods and was raised from under the mould, with the pins facing towards the ECM sheet, using the guide holes and guide rods to align. The assembly was placed in an arbour press and was compressed. The assembly was removed from the arbour press, the pin block retracted and removed, the clamps and hold down plate removed, and the separation slip removed. The free ends of the lugs of the first lug sheet were flattened along the top of the pierced sheet in the direction they originally faced.

The second lug sheet was placed on top of the pierced sheets with the free end of the lugs at an angle of 180° relative to the first lug sheet, guiding the four guide holes down the guide rods to align. The lug sheet was rehydrated with a saline solution. The separation slip and hold down plate were replaced. A spacer block was placed over the hold down plate and clamps were replaced. A pin block comprising an acetal block with a 20 row by 20 column array of blunted pins, arranged in a grid matching that of the clearance holes was used. The pin block also had guide holes aligning with the guide rods and was lowered on top of the hold down plate, with the pins facing towards the ECM sheet, using the guide holes and guide rods to align. The assembly was placed in an arbour press and was compressed. The pin block was retracted and compressed in an arbour press a further two times. The assembly was removed from the arbour press and disassembled. The construct was cut from the mould using a scalpel. This produced a 100 mm×100 mm interlocked laminate graft construct which was moist and very flexible with the appearance of a thick rough sheet without protrusions.

Example 9: 3D Hand Laminated Product

Sheets of ECM were prepared as described in Example 1. A lug sheet was prepared by the following method: eight 5 mm diameter holes were punched into one sheet of lyophilised ECM, measuring 140 mm×240 mm using a cutting die and press, four down one side at centres of 10 mm from the long edge and at centres of 10 mm, 111.5 mm, 130 mm and 231.5 mm from one short side, and four down the only long side in mirror to the first. This sheet was placed to the left over a 140 mm×140 mm flat acetal plate with four 5 mm diameter guide rods positioned equidistant from each corner to match the holes cut into the left end of the lyophilised ECM sheet, the guide rods fixing the position of the ECM on the plate. The plate has a 29 row by 29 column grid of 3.1 mm diameter clearance holes positioned at 3.5 mm centres at its centre, resulting in a perimeter section without holes of around 20 mm wide. This plate functioned as a mould. A hold down plate with guide holes for the lug cutters and matching the pattern of clearance holes was placed on top of the lyophilised ECM sheet. Clamps were applied to secure the assembly together. A 5 mm thick spacer plate with clearance hole size and pattern matching the guide rod holes and the clearance holes was placed on top of the hold down plate. A lug cutting block comprising an acetal block with 2.5 mm diameter circular tube lug cutters spaced at centres of 3.5 mm, matching the pattern of clearance holes was used, using guide rod holes in the acetal block and the lug cutter guide holes to align the lug cutting block when pushing the lug cutters through the ECM sheet. The assembly was placed in an arbour press and was compressed. The lug cutting block was retracted and removed, rotated 180 degrees and replaced. The assembly was placed into an arbour press and compressed. The lug cutting block and spacer was removed. The lug cutting block was rotated 90 degrees and replaced. The so formed lug sheet, with lugs of around 2.8 mm wide covering around a 100 mm×100 mm square, was removed from the tooling then repositioned so that the right hand side of the sheet was over the mould. The sheet was lowered down the guide rods, the hold down plate put into position, the assembly made secure with clamps and a spacer block put into position. The lug cutter block was lowered into position with the same orientation as used when cutting the left hand side of the ECM sheet. The assembly was placed in an arbour press and was compressed. The lug cutting block was retracted and removed, rotated 180 degrees and replaced. The assembly was placed into an arbour press and compressed. The lug cutting block was retracted and, together with the spacer, removed. The lug cutting block was rotated 90 degrees and replaced. The so formed lug sheet, with lugs of around 2.8 mm wide covering around a 100 mm×200 mm rectangle, was removed from the tooling.

Pierced sheets were prepared by the following method: A sheet of fresh ECM was stretched over a 140 mm diameter by 70 mm high semi-spherical hollowed acetal block densely populated with 2.0 mm holes perpendicular to the semi-spherical surface, positioning the ECM sheet to take best advantage of any natural 3D form it possessed. The sheet of ECM was held in the stretched position by an array of securing pins on the underside of the block. This block had the function of a mould. Three more ECM sheets were applied, one at a time, in the same manner.

The conformed interlocked laminated graft construct was assembled by the following method: The long lug sheet was partially hydrated, until it became flexible, and was placed on top of and stretched over the wet ECM sheets. Working along a row of lugs with two size 11 embroidery needles, each lug was lifted, a pierce was made through the four ECM layers, pushing the needle into the closest available hole in the mould, and the lug pushed through the pierce with a blunt pin. The other rows within the area required to be lugged were treated in the same fashion. A scalpel was used to cut the device away from the mould. The laminated graft product was moist and flexible with the appearance of a thick rough sheet, and conformed to the shape of the mould.

Example 10: 3D Single Point Laminated Product

Sheets of ECM were prepared as described in Example 1. A lug sheet was prepared by the following method: eight 5 mm diameter holes were punched into one sheet of lyophilised ECM, measuring 140 mm×240 mm using a cutting die and press, four down one side at centres of 10 mm from the long edge and at centres of 10 mm, 111.5 mm, 130 mm and 231.5 mm from one short side, and four down the only long side in mirror to the first. This sheet was placed to the left over a 140 mm×140 mm flat acetal plate with four 5 mm diameter guide rods positioned equidistant from each corner to match the holes cut into the left end of the lyophilised ECM sheet, the guide rods fixing the position of the ECM on the plate. The plate has a 29 row by 29 column grid of 3.1 mm diameter clearance holes positioned at 3.5 mm centres at its centre, resulting in a perimeter section without holes of around 20 mm wide. This plate functioned as a mould. A hold down plate with guide holes for the lug cutters and matching the pattern of clearance holes was placed on top of the lyophilised ECM sheet. Clamps were applied to secure the assembly together. A 5 mm thick spacer plate with clearance hole size and pattern matching the guide rod holes and the clearance holes was placed on top of the hold down plate. A lug cutting block comprising an acetal block with 2.5 mm diameter circular tube lug cutters spaced at centres of 3.5 mm, matching the pattern of clearance holes was used, using guide rod holes in the acetal block and the lug cutter guide holes to align the lug cutting block when pushing the lug cutters through the ECM sheet. The assembly was placed in an arbour press and was compressed. The lug cutting block was retracted and removed, rotated 180 degrees and replaced. The assembly was placed into an arbour press and compressed. The lug cutting block and spacer was removed. The lug cutting block was rotated 90 degrees and replaced. The so formed lug sheet, with lugs of around 2.8 mm wide covering around a 100 mm×100 mm square, was removed from the tooling then repositioned so that the right hand side of the sheet was over the mould. The sheet was lowered down the guide rods, the hold down plate put into position, the assembly made secure with clamps and a spacer block put into position. The lug cutter block was lowered into position with the same orientation as used when cutting the left hand side of the ECM sheet. The assembly was placed in an arbour press and was compressed. The lug cutting block was retracted and removed, rotated 180 degrees and replaced. The assembly was placed into an arbour press and compressed. The lug cutting block was retracted and, together with the spacer, removed. The lug cutting block was rotated 90 degrees and replaced. The so formed lug sheet, with lugs of around 2.8 mm wide covering around a 100 mm×200 mm rectangle, was removed from the tooling.

Pierced sheets were prepared by the following method: A sheet of fresh ECM was stretched over a 140 mm diameter by 70 high semi-spherical hollowed acetal block populated with 2.5 mm holes perpendicular to the semi-spherical surface and in a pattern that proved a dense array of holes, positioning the ECM sheet to take best advantage of any natural 3D form it possessed. The sheet of ECM was held in the stretched position by an array of securing pins on the underside of the block. This block had the function of a mould. Three more ECM sheets were applied, one at a time, in the same manner. A robotic arm was used to pierce the sheets.

The conformed interlocked laminated graft construct was assembled by the following method: The long lug sheet was partially hydrated, until it became flexible, and was placed on top of and stretched over the wet ECM sheets, aligning the lugs around the perimeter of the area required to be lugged over the pierced holes. A robotic arm was used to push each lug through the respective piercing using a blunt pin tool. A scalpel was used to cut the device away from the mould. The laminated graft product was moist and flexible with the appearance of a thick rough sheet, and conformed to the shape of the mould.

Example 11: 3D Multi-Point Laminated Product

Sheets of ECM were prepared as described in Example 1. A lug sheet was prepared by the following method: eight 5 mm diameter holes were punched into one sheet of lyophilised ECM, measuring 140 mm×240 mm using a cutting die and press, four down one side at centres of 10 mm from the long edge and at centres of 10 mm, 111.5 mm, 130 mm and 231.5 mm from one short side, and four down the only long side in mirror to the first. This sheet was placed to the left over a 140 mm×140 mm flat acetal plate with four 5 mm diameter guide rods positioned equidistant from each corner to match the holes cut into the left end of the lyophilised ECM sheet, the guide rods fixing the position of the ECM on the plate. The plate has a 29 row by 29 column grid of 3.1 mm diameter clearance holes positioned at 3.5 mm centres at its centre, resulting in a perimeter section without holes of around 20 mm wide. This plate functioned as a mould. A hold down plate with guide holes for the lug cutters and matching the pattern of clearance holes was placed on top of the lyophilised ECM sheet. Clamps were applied to secure the assembly together. A 5 mm thick spacer plate with clearance hole size and pattern matching the guide rod holes and the clearance holes was placed on top of the hold down plate. A lug cutting block comprising an acetal block with 2.5 mm diameter circular tube lug cutters spaced at centres of 3.5 mm, matching the pattern of clearance holes was used, using guide rod holes in the acetal block and the lug cutter guide holes to align the lug cutting block when pushing the lug cutters through the ECM sheet. The assembly was placed in an arbour press and was compressed. The lug cutting block was retracted and removed, rotated 180 degrees and replaced. The assembly was placed into an arbour press and compressed. The lug cutting block and spacer was removed. The lug cutting block was rotated 90 degrees and replaced. The so formed lug sheet, with lugs of around 2.8 mm wide covering around a 100 mm×100 mm square, was removed from the tooling then repositioned so that the right hand side of the sheet was over the mould. The sheet was lowered down the guide rods, the hold down plate put into position, the assembly made secure with clamps and a spacer block put into position. The lug cutter block was lowered into position with the same orientation as used when cutting the left hand side of the ECM sheet. The assembly was placed in an arbour press and was compressed. The lug cutting block was retracted and removed, rotated 180 degrees and replaced. The assembly was placed into an arbour press and compressed. The lug cutting block was retracted and, together with the spacer, removed. The lug cutting block was rotated 90 degrees and replaced. The so formed lug sheet, with lugs of around 2.8 mm wide covering around a 100 mm×200 mm rectangle, was removed from the tooling.

Pierced sheets were prepared by the following method: A sheet of fresh ECM was stretched over a 140 mm diameter by 70 high semi-spherical hollowed acetal block populated with sections of 2.5 mm holes that were parallel to one another and in a pattern that proved a dense array of holes, positioning the ECM sheet to take best advantage of any natural 3D form it possessed. The sheet of ECM was held in the stretched position by an array of securing pins on the underside of the block. This block had the function of a mould. Three more ECM sheets were applied, one at a time, in the same manner. A robotic arm was used to pierce the sheets. The mould was indexed on a stand and a needle block containing 56 size 11 embroidery needles was applied to the wet ECM, at two positions, at each index resulting in the ECM becoming pierced with regular pattern over the area to be lugged.

The conformed interlocked laminated graft construct was assembled by the following method: The long lug sheet was partially hydrated, until it became flexible, and was placed on top of and stretched over the wet ECM sheets, aligning the lugs around the perimeter of the area required to be lugged over the pierced holes. The mould was indexed on a stand and a pin block containing 56 blunt pins arranged in the same pattern as for the holes in the mould was applied to the wet ECM, at two positions, at each index resulting in the ECM becoming lugged over the area to be lugged. A scalpel was used to cut the device away from the mould. The laminated graft product was moist and flexible with the appearance of a thick rough sheet, and conformed to the shape of the mould.

Example 12: Wet Handling Integrity Test of
Lugged Ovine Forestomach Matrix Laminate and
Equivalent Non-Lugged Laminates A freeze dried lugged laminate comprising one lug sheet and two pierced sheets was prepared according to Example 1, and freeze dried. An equivalent non-lugged 3-ply laminate was prepared by lamination, in accordance with the method of Floden et al. (8). Ovine forestomach matrix was prepared in accordance with the procedure described in U.S. Pat. No. 8,415,159. One layer of wet ovine forestomach matrix was placed on a flat surface with the abluminal surface facing up. A second layer was placed on top the first layer, with the smooth abluminal surface facing down, contacting the first layer. A third layer was placed on top of the second layer, with the smooth abluminal surface facing upward. Pressure was applied to remove any voids between the layers. The three-ply laminate was then lyophilised to create a three layer laminate.

Figure 6:
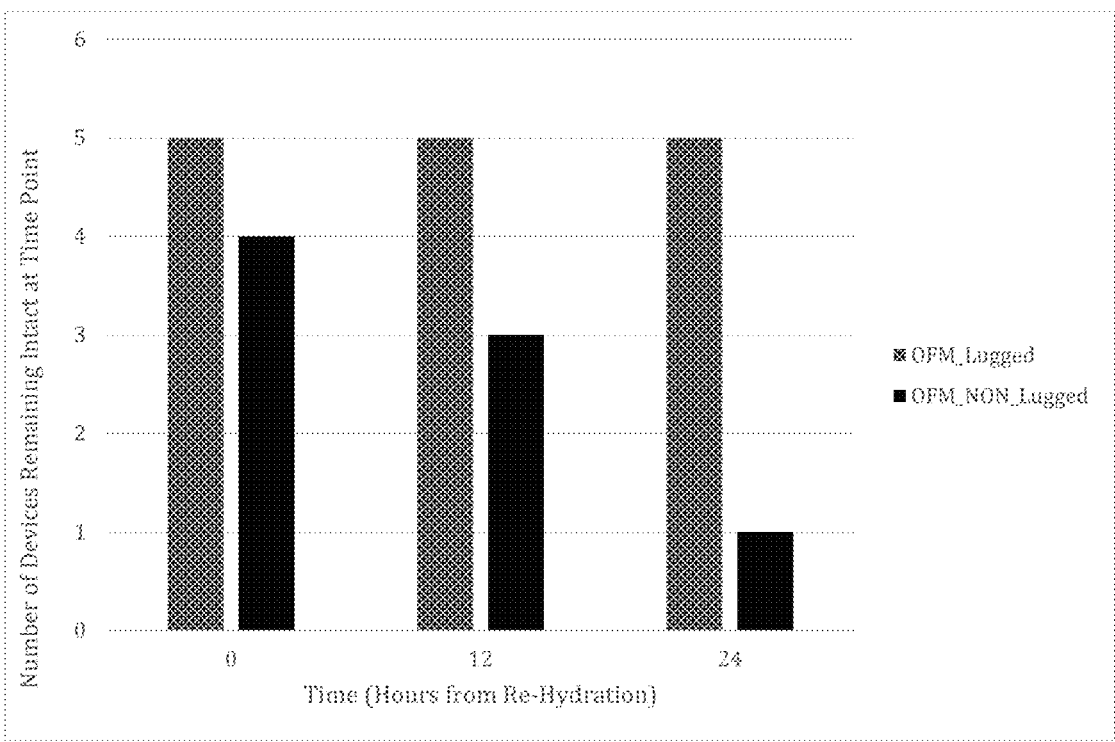
FIG. 6 is a histogram showing the wet handling integrity of lugged and non-lugged ovine forestomach matrix.

To compare the lamination strength of the lugged and equivalent non-lugged laminates a wet handling simulation test was performed. Both the lugged and non-lugged laminates were cut into 4 cm×4 cm samples prior to the wet handling test. The final sample size for testing of each of the laminates was five (n=5). Ten petri dishes were each filled with 20 mL of 1×PBS. At time point T=0 hours, a 4 cm×4 cm laminate (lugged or non-lugged) was introduced to a petri dish and allowed to fully rehydrate in 1×PBS prior to the wet handling test. Upon rehydration the laminate was picked up at a corner with forceps and shaken for five seconds using a side to side motion. The laminate was then re-introduced to the PBS and folded into quarters. While still folded, the laminate was then dropped from a height of 20 cm into the lid of petri dish. The laminate was then re-introduced to the PBS and shaken for a further 5 seconds. On completion of testing the extent to which the samples delaminated was assessed. Delamination was defined as 'more than 50% of any layer became detached from the opposing layer'. Samples that delaminated following the wet handling simulation scored as 'fail'. Wet handling simulation testing was undertaken at times T=0 hours, T=12 hours and 24 hours. Laminates remained submerged and hydrated in PBS for the duration of the test. The results from the wet handling simulation test are shown in FIG. 6.

Figure 7:
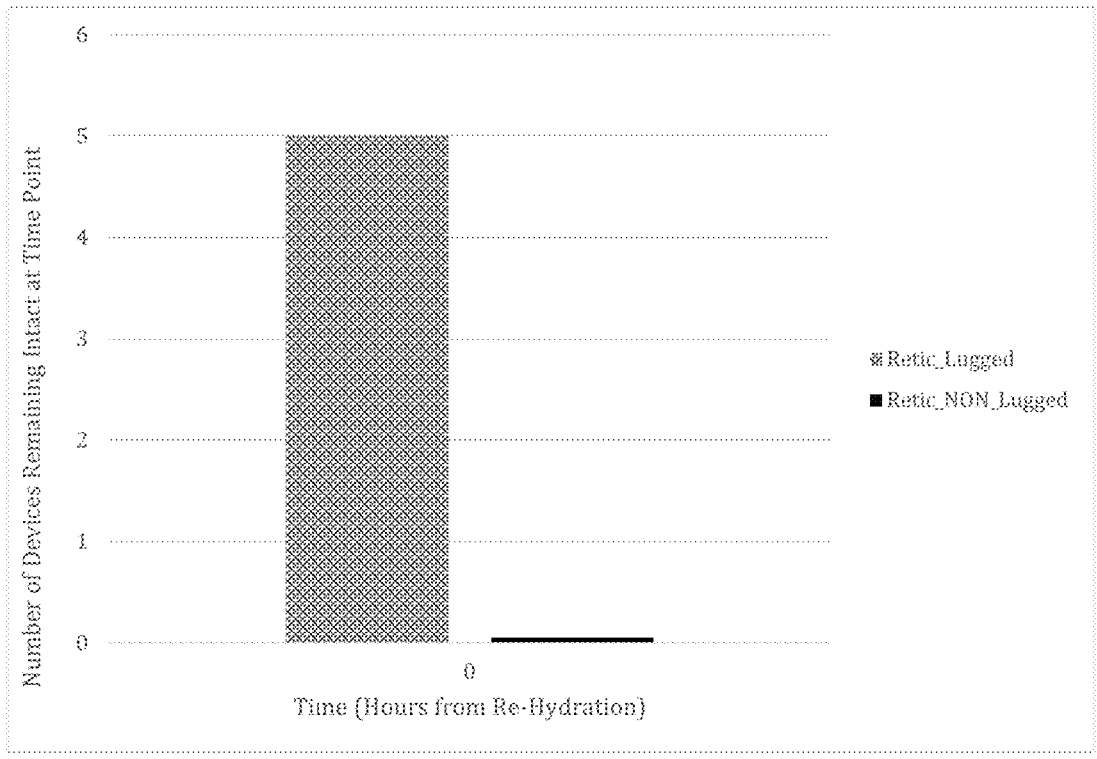
FIG. 7 is histogram showing the wet handling integrity of lugged and non-lugged ovine reticulum matrix.

Example 13: Wet Handling Simulation Test of
Ovine Reticulum Lugged Laminates and Equivalent
Non-Lugged Laminates Ovine reticulum ECM was prepared as follows. Ovine reticulum tissue was sourced from sheep, less than 1 year old. The muscle layer was physically separated from the tissue and discarded. The remaining tissue (approx. 1500 g) was incubated in 0.1% Triton TX-100 (10 L), with shaking at room temperature for four hours. The solution was discarded. The tissue was incubated in a solution comprising 0.1% TX-100, 0.3% TRIS and 0.15% EDTA (10 L) for 18 hours at room temperature. The solution was discarded. The tissue was finally rinsed in purified water (10 L) for 10 min, three times at room temperature, with shaking. The decellularised material was freeze dried as required. A freeze dried lugged laminate comprising one lug sheet and two pierced sheets was prepared according to Example 1, and freeze dried. An equivalent non-lugged 3-ply laminate was prepared by according to Example 12. The wet handling simulation test was conducted according to Example 12 to compare the lamination strength of the lugged and equivalent non-lugged laminates. The results for both lugged and non-lugged ovine reticulum ECM laminates are shown in FIG. 7. Ovine reticulum lugged laminates did not remain intact after initial handling (T=0).

Figure 8:
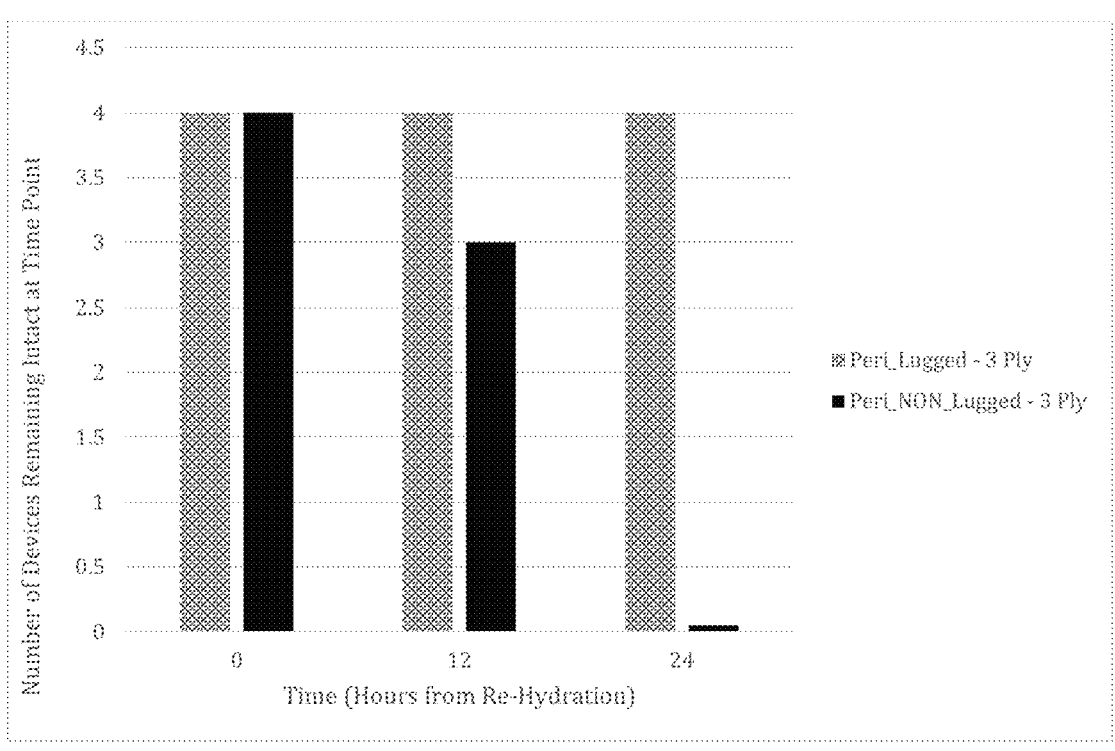
FIG. 8 is histogram showing the wet handling integrity of lugged and non-lugged ovine pericardium matrix.

Example 14: Wet Handling Integrity Test of Ovine
Pericardium Lugged Laminates and Equivalent
Non-Lugged Laminates Ovine pericardium ECM was prepared for lamination as follows. Ovine pericardium was sourced from sheep, less than 1 year old. The pericardial sac was dissected from the heart and lungs and frozen to assist with fat removal from the tissue. Upon thawing, the tissue was then cleaned and de-ephithelialised according to Example 13. A freeze dried pericardium laminate comprising one lug sheet and two pierced sheets was prepared according to Example 1 and freeze dried. An equivalent non-lugged 3-ply laminate was prepared by according to Example 12. Notably, the pericardium geometry meant smaller devices than those of Examples 1 and 12. Both laminates were cut into 2 cm×2 cm laminates prior to the wet handling test. Final sample size for each laminate type was four (n=4). The wet handling simulation test was conducted according to Example 12. The results are shown in FIG. 8.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

REFERENCES

1. Schenke-Layland K, Xie J, Heydarkhan-Hagvall S, Hamm-Alvarez S F, Stock U A, Brockbank K G M, et al. Optimized Preservation of ECM in Cardiac Tissues:

Implications for Long-Term Graft Durability. Ann Thorac Surg. 2007 May; 83(5):1641-50.

2. Schenke-Layland K, Madershahian N, Riemann I, Starcher B, Halbhuber K-J, König K, et al. Impact of Cryopreservation on ECM Structures of Heart Valve Leaflets. Ann Thorac Surg. 2006 March; 81(3):918-26.

3. Crapo P M, Gilbert T W, Badylak S F. An overview of tissue and whole organ decellularization processes. Biomaterials. 2011 April; 32(12):3233-43.

4. Davidenko N, Gibb T, Schuster C, Best S M, Campbell J J, Watson C J, et al. Biomimetic collagen scaffolds with anisotropic pore architecture. Acta Biomater. 2012 February; 8(2):667-76.

5. Konstantinovic M L, Lagae P, Zheng F, Verbeken E K, De Ridder D, Deprest J A. Comparison of host response to polypropylene and non-cross-linked porcine small intestine serosal-derived collagen implants in a rat model. BJOG Int J Obstet Gynaecol. 2005; 112(11):1554-60.

6. Chu C C. The effect of pH on the in vitro degradation of poly(glycolide lactide) copolymer absorbable sutures. J Biomed Mater Res. 1982; 16(2):117-24.

7. Chu C C. A comparison of the effect of pH on the biodegradation of two synthetic absorbable sutures. Ann Surg. 1982 January; 195(1):55-9.

8. Floden E W, Malak S F, Basil-Jones M M, Negron L, Fisher J N, Lun S, Dempsey S G, Haverkamp R G, Ward B R and May B C (2010). Biophysical characterization of ovine forestomach extracellular matrix biomaterials. J Biomed Mater Res B Appl Biomater 96(1): 67-75.

The invention claimed is:

1. A method of preparing a tissue graft product, comprising the step of laminating two or more sheets of material together by interlocking portions of one sheet with portions of another sheet, wherein each sheet comprises extracellular matrix (ECM) or polymeric material, comprising the steps of:

(i) placing a first sheet of material having multiple lugs over a second sheet of material having multiple holes, and (ii) pushing the lugs of the first sheet through the holes in the second sheet, the holes and the lugs having dimensions to interlock the first sheet with the second sheet, and wherein each lug comprises a section of the first sheet that is cut from the first sheet and remains connected to the first sheet.

2. The method of claim 1, wherein the lugs of the first sheet engage with a surface of the second sheet.

3. The method of claim 1, wherein the sheets are dried sheets.

4. The method of claim 1, further comprising the step of:

positioning a third sheet between the first sheet and the second sheet, wherein the third sheet comprises multiple holes aligned with holes of the second sheet, and wherein the lugs of the first sheet extend through the holes in the third sheet to interlock the first sheet with the second and third sheets.

5. The method of claim 1, further comprising the step of:

positioning a third sheet comprising multiple lugs aligned with holes of the second sheet, and pushing the lugs of the third sheet through the holes in the second sheet to interlock the third sheet with the second sheet.

6. The method of claim 5, wherein each lug of the first sheet is interlocked with the third sheet and each lug of third sheet is interlocked with the first sheet.

7. The method of claim 5, wherein the third sheet comprises multiple lugs and the first sheet comprises multiple holes, wherein the lugs of the first sheet are offset from the lugs of the third sheet.

8. The method of claim 1, wherein at least one sheet comprises ECM.

9. The method of claim 8, wherein the ECM is formed from the propria-submucosa of the forestomach of a ruminant.

10. The method of claim 1, wherein at least one sheet comprises a synthetic polymeric material.

11. The method of claim 10, wherein the synthetic polymeric material is formed from polypropylene, polytetrafluoroethylene, polyglycolic acid, polylactic acid, poliglecaprone-25, or polyester.

12. The method of claim 1, wherein at least one sheet comprises a natural polymeric material.

13. The method of claim 12, wherein the natural polymeric material is a protein, polysaccharide, glycoprotein, proteoglycan, or glycosaminoglycan.

14. The method of claim 1, wherein the tissue graft product is a substantially flat sheet or has a 3-dimensional form shaped to conform to a location to which the product is to be grafted.

* * * * *